United States Patent
Park et al.

(10) Patent No.: US 7,998,698 B2
(45) Date of Patent: Aug. 16, 2011

(54) METHOD FOR PREDICTING SUSCEPTIBILITY TO RADIATION PNEUMONITIS

(75) Inventors: Young-Mee Park, Williamsville, NY (US); Gary Y. Yang, E. Amherst, NY (US); Nithya Ramnath, E. Amherst, NY (US)

(73) Assignee: Health Research Inc., Buffalo, NY (US)

( * ) Notice: Subject to any disclaimer, the term of this patent is extended or adjusted under 35 U.S.C. 154(b) by 1111 days.

(21) Appl. No.: 11/809,250

(22) Filed: May 31, 2007

(65) Prior Publication Data
US 2008/0004243 A1    Jan. 3, 2008

Related U.S. Application Data

(60) Provisional application No. 60/810,072, filed on May 31, 2006.

(51) Int. Cl.
*A61K 31/66* (2006.01)
*A61K 31/4045* (2006.01)
*A61K 31/522* (2006.01)
*A61P 39/00* (2006.01)
*C12Q 1/28* (2006.01)

(52) U.S. Cl. ........ 435/25; 435/28; 514/263.36; 514/419

(58) Field of Classification Search .................... 435/25, 435/28

See application file for complete search history.

(56) References Cited

U.S. PATENT DOCUMENTS
5,389,522 A * 2/1995 Repine et al. .................. 435/7.4

FOREIGN PATENT DOCUMENTS
WO    WO-03/016527    *    2/2003

OTHER PUBLICATIONS de Haan et al., Human Molecular Genetics 1996, 5(2), 283-292.*
Epperly et al., Radiation Research 2000, 154: 365-374.*
Beinert et al.; "Oxidant-induced lung injury in anticancer therapy"; Eur J Medical Research, Feb. 25, 1999, vol. 4, Issue 2; pp. 43-53; Abstract only available.
de Haan, et al.; "Cu/Zn-superoxide dismutase and glutathione peroxidase during aging"; Biochem Mol Biol Int., May 1995, vol. 35, Issue 6; pp. 1281-1297; Abstract only available.
Yang, et al.; "High Superoxide Dismutase (SOD) and Low Glutathione Peroxidase (GPX) Activities in Red Blood Cells (RBCs) Predict Susceptibility of Lung Cancer Patients to Radiation Pneumonitis"; International Journal of Radiation Oncology Biology Physics, Nov. 1, 2006 (available online Oct. 12, 2006), vol. 66, Issue 3, Supp. 1; pp. S463-S464; Abstract No. 2458.
Comhair, et al.; "Antioxidant responses to oxidant-mediated lung diseases"; Am. J Physiol. Lung Cell. Mol. Physiol., 2002, vol. 283; pp. L246-L255.

* cited by examiner

*Primary Examiner* — Ralph Gitomer
*Assistant Examiner* — Robert Yamasaki
(74) *Attorney, Agent, or Firm* — Hodgson Russ LLP

(57) ABSTRACT

Provided is a method for determining whether an individual is likely to be susceptible to radiation pneumonitis from radiation therapy and for developing a treatment based on the determination of susceptibility. The method involves measuring SOD and GPX activity levels. A high SOD or low GPX activity, or a combination thereof, is indicative that the individual is likely to be susceptible to radiation pneumonitis.

20 Claims, 3 Drawing Sheets

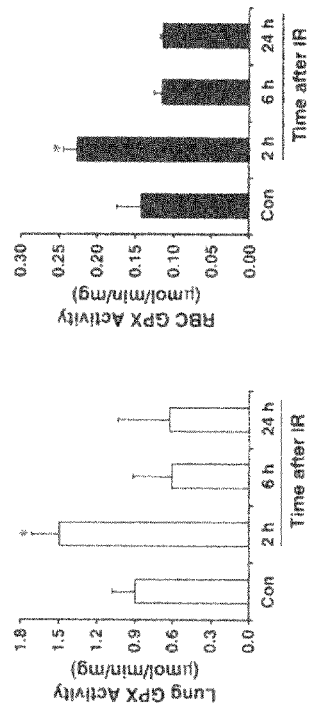
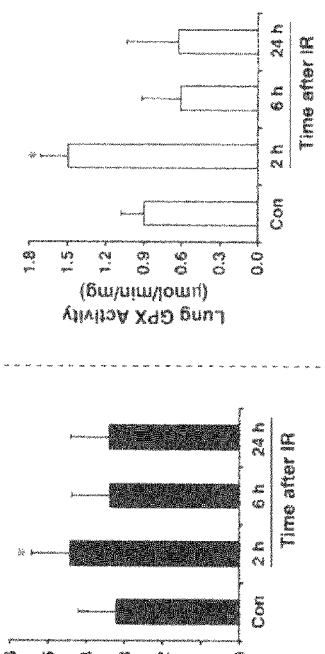
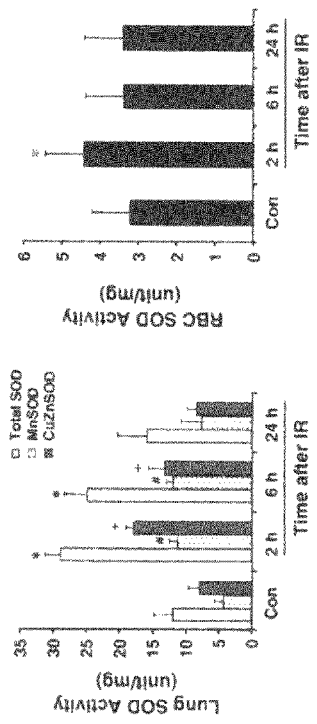
Figure 1A
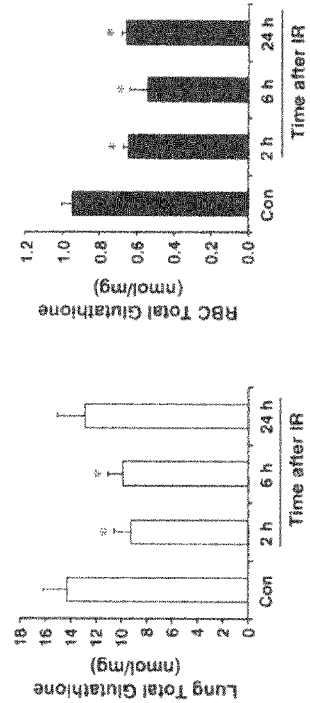
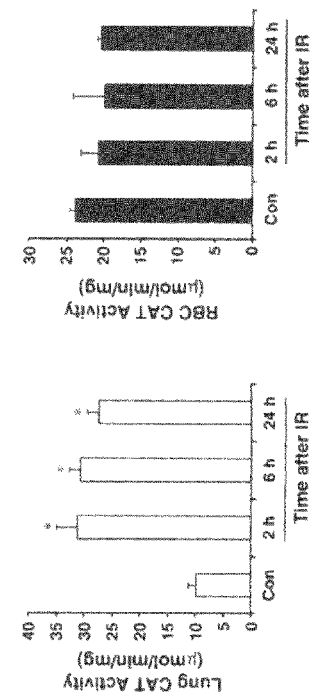
Figure 1B
Figure 1C
Figure 1D

METHOD FOR PREDICTING SUSCEPTIBILITY TO RADIATION PNEUMONITIS

This application claims priority to U.S. Provisional Application Ser. No. 60/810,072, filed May 31, 2006, the entire disclosure of which is incorporated herein by reference.

This work was supported by National Institutes of Health Grant Nos. CA109480 and CA16056. The government has certain rights in this invention.

FIELD OF THE INVENTION

The present invention relates generally to treatment of cancer and specifically to identifying cancer patients at risk for pneumonitis associated with radiation therapy.

BACKGROUND OF THE INVENTION

Radiotherapy (RT) is a frequent treatment modality for cancer patients. The goal of RT is to deliver a cytotoxic dose to the tumor, while minimizing the radiation exposure to the surrounding normal tissues. However, radiation pneumonitis is a serious and potentially lethal treatment-related complication of RT, and RT-induced pneumonitis is one of the most serious dose-limiting toxicities, particularly for patients receiving RT for lung cancer. The incidence of symptomatic radiation pneumonitis ranges from roughly 10% to 30% with radiotherapy or chemoradiotherapy (Robnett T J et al. (2000) Int J Radiat Oncol Biol Phys Vol. 48, pp 89-94; Seppenwoolde Y et al. (2003) Int J Radiat Oncol Biol Phys Vol. 55, pp 724-735). Symptoms of pneumonitis generally do not appear until at least 1 to 3 months after the completion of treatment. Late fibrosis might also develop months to years post-therapy. Lung fibrosis is the permanent scarring of lung tissue that occurs more gradually (over months to years) in response to the initial tissue injury and leads to permanent impairment of oxygen transfer. Chemotherapy administered with RT is expected to provide systemic control as well as to enhance loco-regional control via radiation sensitization. While the benefit of this combination therapy has been supported by several studies [Dillman, et al. (1996) *J Natl. Cancer Inst.* Vol. 88, pp 1210-1215; Furuse, et al. (1999) *J. Clin. Oncol.* Vol. 17, pp 2692-2699], it is unfortunately achieved at the expense of increased acute normal tissue toxicity [Byhardt, et al. (1998) *Int. J. Radiat. Oncol. Biol. Phys.* Vol. 42, pp 469-478; Bradley, et al. (2005) *Int. J. Radiat. Oncol. Biol. Phys.* Vol. 61, pp 318-328].

At present, no generally accepted method is available to predict an individual's risk of developing radiation pneumonitis. Therefore, there is a need for a method of determining whether a cancer patient is likely to be susceptible to radiation pneumonitis. Such a method would facilitate treatment modifications to minimize the extent of radiation injury as well as to offer possible early radiation pneumonitis preventive intervention.

SUMMARY OF THE INVENTION

The present invention provides a method for identifying an individual as likely to be susceptible to radiation pneumonitis. The method comprises obtaining a biological sample comprising red blood cells from the individual and determining the amount of glutathione peroxidase (GPX) activity and/or superoxide dismutase (SOD) activity in the sample. Low GPX or high SOD activity relative to a normal control is indicative that the individual is likely to be susceptible to radiation pneumonitis. The invention also takes advantage of the discovery that the ratio of GPX/SOD activity is a powerful predictor of susceptibility to radiation pneumonitis. In particular, a low GPX/SOD ratio relative to a normal control is indicative that the individual is likely to be susceptible to radiation pneumonitis.

The invention also permits determination of a treatment regime for a cancer patient, since normal levels of GPX and SOD indicate that the individual is a candidate for aggressive radiation therapy, while those individuals identified as susceptible to radiation pneumonitis can be treated using smaller radiation dosages, more focused radiation, no RT, or other modifications to RT that are known to those skilled in the art.

BRIEF DESCRIPTION OF THE DRAWINGS

FIGS. 1A-1D provide graphical representations of changes of SOD, GPX, and CAT activities and glutathione content of C3H/HeN mice after whole body irradiation. For these figures, Mice were irradiated at a single fraction of 10 Grays (Gy). SOD (total, MnSOD, and CuZnSOD) (FIG. 1A), GPX (FIG. 1B), and CAT (FIG. 1C) activities of lung (left panel) were determined at 2, 6, and 24 h after irradiation. SOD (FIG. 1A), GPX (FIG. 1B), and CAT (FIG. 1C) activities of RBC (right panel) were also determined at the same time points. Total glutathione contents (FIG. 1D) of the lung tissue and RBC are expressed as the GSH equivalent to the sum of GSH+2GSSG. Results are expressed as means±standard deviations (n=10). Significance of the differences was determined by using the Student t test. * $P<0.05$, #$P<0.05$, or +$P<0.05$ vs unirradiated control (Con).

DETAILED DESCRIPTION OF THE INVENTION

Figure 2B:
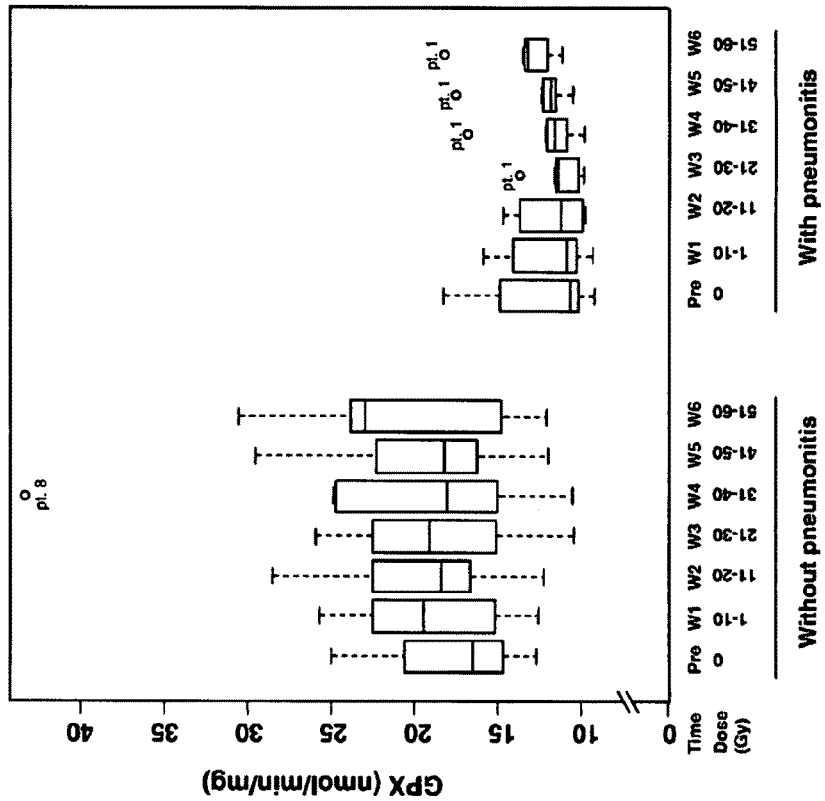
FIGS. 2A and 2B provide graphical representations of comparisons of SOD and GPX activities of lung cancer patients without pneumonitis versus those who developed pneumonitis. SOD (FIG. 2A) and GPX (FIG. 2B) activities of red blood cells (RBCs) were plotted separately for patients without pneumonitis and with pneumonitis. The boxes indicate the 25th and the 75th percentile (the lower and upper edge, respectively), and the lines within the boxes represent the median. Median numeric values and number of patients evaluated at each time point are shown in Table 2. The points at the ends of the whiskers are the greatest or the smallest points that are not outliers. Outliers (circles) were plotted individually with a patient serial number.

The present invention provides a method for identifying an individual as likely to be susceptible to radiation pneumonitis. Radiation pneumonitis is a well recognized condition that can be diagnosed by one skilled in the art according to conventional parameters, such as those established by the Radiation Therapy Oncology Group (RTOG) or the European Organization for Research and Treatment of Cancer (EORTC) guidelines. The present method is based on the discovery that in human patients, as well as in a pneumonitis-sensitive C3H/HeN mouse model, differences in SOD and GPX activity are predictive of whether an individual is likely to develop radiation pneumonitis in response to RT. By measuring the activity of these enzymes in lung tissue and RBCs from the mice, as well as in RBCs from humans who have been treated with RT, striking differences in the activities of these enzymes that predict susceptibility to development of radiation pneumonitis have been discovered. In particular, those human patients who developed radiation pneumonitis showed higher SOD and lower GPX activities at baseline compared to those who did not develop radiation pneumonitis. This imbalance of SOD and GPX activity was displayed consistently throughout the RT treatment period. The sensitivity and specificity of pneumonitis prediction were further increased when the GPX/SOD activity ratio was analyzed. Thus, the invention provides a powerful tool comprising monitoring SOD and GPX activities to identify patients who are likely to be susceptible to radiation pneumonitis. Accordingly, individuals who are not likely to be susceptible to radiation pneumonitis can also be identified by the method of the invention.

The method comprises obtaining a biological sample comprising red blood cells from an individual and determining the enzymatic activity of GPX, SOD, or a combination thereof. Determining low GPX activity or high SOD activity relative to a normal control indicates that the individual is likely to be susceptible to radiation pneumonitis if treated with RT. Determining GPX or SOD activities that are the same as a normal control, or an SOD activity that is lower than a normal control, or a GPX activity that is higher than a normal control, are indicative that the individual is not likely to be susceptible to radiation pneumonitis.

Determining enzymatic values for GPX and SOD can be performed according to conventional techniques that are well know to those skilled in the art. Some examples of such techniques are disclosed in Park, et al. (2001) *J. Biol. Mol. Biochem*. Vol. 34, pp 544-550, and Park, et al (1998) *Free Radic. Biol. Med*. Vol. 25, pp 79-86, from which the descriptions for determining enzymatic activity are incorporated herein by reference.

The present method can be performed by measuring GPX or SOD activity levels, or combinations thereof, from an individual and comparing the activities to a normal control. A "normal control" means GPX and SOD enzyme activities determined from individuals who do not develop radiation pneumonitis after RT. A normal control can be provided in various forms, such as a standardized curve, average SOD and GPX enzymatic activities determined from individuals who do not develop radiation pneumonitis after RT, or a range of enzyme activities characteristic of individuals who do not develop radiation pneumonitis after RT. These same measurements can be used to establish normal controls for a ratio of GPX/SOD enzymatic activity. Representative values for GPX and SOD activities for individuals who develop or do not develop radiation pneumonitis are presented in the Examples and Figures herein. Some examples of such enzyme activities include but are not limited to a GPX activity of less than 14.7 μmol/min/mg and an SOD activity of 6.4 units/mg or greater, which are each indicative that an individual is likely to be susceptible to radiation pneumonitis.

In one embodiment, the ratio of GPX/SOD activity is used as an indicator of whether an individual is likely to be susceptible to radiation pneumonitis. In this embodiment, a low GPX/SOD ratio relative to a normal control is indicative that the individual is likely to be susceptible to radiation pneumonitis. Examples of such ratios include but are not limited to ratios of about 0.5 GPX/SOD activity, or lower ratios. It will be recognized by those skilled in the art that determining the inverse ratio (i.e., SOD/GPX activity) is an alternative and functionally equivalent measurement for use in the present invention.

The enzymatic activities of GPX and SOD can be determined from any biological sample that comprises red blood cells (RBCs). RBCs can be isolated from an individual using well known conventional methods. The biological sample comprising RBCs can be obtained from the individual and analyzed before, during or after administering RT.

Since it is recognized that radiation pneumonitis is caused by RT, the invention is expected to be suitable for use with individuals who are potential candidates for RT for any type of cancer that is a primary cancer in the thorax or that has metastasized to the thorax. Non-limiting examples of such cancers include, for example, solid tumors, such as lung (small cell and non-small cell), esophageal, prostate, breast, colorectal, ovarian, melanoma, urinary system, uterine, endometrial, pancreatic, head and neck, oral cavity, thyroid, stomach, brain and other nervous system, and liver tumors, and/or hematological cancers, such as Hodgkins Lymphoma, Non-Hodgkins Lymphoma (NHL), chronic and other leukemias, and myeloma, including those hematological disorders where an individual is a potential candidate for whole-body irradiation, such as an individual who is a candidate for bone marrow replacement.

In another embodiment, determining that an individual is or is not likely to be susceptible to radiation pneumonitis permits determination of a treatment regime that can be used in making a treatment recommendation and for treating the patient. For example, conventionally fractionated RT for non-small cell lung cancer employs 1.8-2.0 Gy fractions given once daily for 5 days each week to a total dose of 60-66 Gy concurrently with chemotherapy. While adequate radiation of a tumor is essential to the success of treatment, the outcome of this radiation dosage to the tumor remains poor, and it has been estimated that as high as 80-100 Gy could be needed to eradicate large tumor masses in lung cancer (Fletcher G. (1973) Br J Radiol S46:1-12). However, the risk for development of radiation pneumonitis has limited attempts to utilize such dosage escalations. Thus, the present invention provides a method for determining susceptibility to radiation pneumonitis that is expected to allow oncologists to individualize radiation treatment volume, dosage, and a choice of adjuvant chemotherapy. For example, identifying patients at low risk of radiation pneumonitis according to the present method is expected to permit escalation of radiation treatment to higher doses to improve the likelihood of eradicating the tumor and to improve patient survival. Further, at present, because of disastrous effects from radiation pneumonitis, treatment breaks or dose reductions are often required, limiting the success of RT. It has also been shown that interrupting RT because of pneumonitis significantly reduces overall survival in lung cancer patients (Jeremic B et al. (2003) Lung Cancer Vol. 40, pp 317-323). Moreover, patients with known risks for radiation pneumonitis because of, for example, infection or a history of cigarette smoking, are usually give lower doses of radiation of between 30-60 Gy, which may be suboptimal for adequate tumor control for certain types of cancer, such as for non-small cell lung cancer. To address this, patients identified by the method of the invention as likely to be susceptible to radiation pneumonitis could be treated with radiation technologies such as intensity-modulated radiotherapy (IMRT) with respiratory-gating, stereotactic radiotherapy, particle-beam therapy with protons or helical tomotherapy to limit the irradiation of normal lung tissue while maintaining similar or improved coverage of the tumor (Suit H. (2002) Int J Radiat Oncol Biol Phys Vol. 53, pp 798-809). An additional alternative is to allow the normal lung tissue to be irradiated but to also administer radiation protector medications with cytoprotective activity that are known to those skilled in the art to reduce the severity of radiation damage. For example, data indicate that amifostine, Angiotensin-Converting Enzyme (ACE) inhibitors, pentoxifylline, or melatonin may enable patients to receive their scheduled doses of radiotherapy with reduced risk of pneumonitis (Antonadou D et al. (2003) J Radiat Oncol Biol Phys Vol. 57, pp 402-408; Wang L W et al. (2000) Radiat Res Vol. 153, pp 405-410; Ozturk B et al. (2004) Int J Radiat Oncol Biol Phys Vol. 5, pp 213-219; Vijayalaxmi et al. (2004) Int J Radiat Oncol Biol Phys Vol. 59, pp 639-653). Accordingly, the present invention is expected to allow physicians to customize therapy, modify therapy intensity, or administer radiation protectors for patients identified as likely to be susceptible or not susceptible to radiation pneumonitis.

The following Examples illustrate but are not intended to limit the present invention.

Example 1

This Example provides a comparison of the antioxidant defense systems of lung tissue and of RBC in radiation pneumonitis-sensitive C3H/HeN mice To obtain the data presented in this Example, male C3H/HeN mice (5 to 6 weeks old) were used. Inbred C3H/HeN mice manifest pulmonary injury patterns similar to those of humans when irradiated [Franko, et al. (1991) Radiat. Res. Vol. 126, pp 349-356; Chiang, et al. (2005) Int J. Radiat. Oncol. Biol. Phys. Vol. 62, pp 862-871]. Whole body irradiation (10 Gy) was performed by using 4 MV photon beams (MeVatron, Siemens, Germany). Irradiation dose was calculated at the mid depth of mice in the field size of 40 cm with a dose rate of 0.2 Gy/min according to standard methods and essentially as previously described [Park, et al. (2001) J. Biol. Mol. Biochem. Vol. 34, pp 544-550]. Mice were sacrificed and the lungs were removed at the specified time after irradiation. The tissues were washed and frozen by freeze-clamping with dry ice-cooled tongs immediately. Blood was drawn by heart puncture into tubes containing 50 μl of anticoagulant citrate dextrose solution (Baxter, Deerfield, Ill.). Red blood cells were separated from plasma by centrifugation (1800 g, 5 min) at 4° C. and washed three times with phosphate-buffered saline. Tissue and RBC samples were stored at −80° C. until analyzed.

To initiate the experiments, the animals were exposed to either sham irradiation or a single fraction of 10 Gy whole body irradiation, and sacrificed 2, 6, and 24 h after irradiation. First, SOD (total, MnSOD, and CuZnSOD), GPX, and CAT activities were measured in the irradiated lung. Enzyme activities were measured following previously described procedures [Park, et al. (2001) J. Biol. Mol. Biochem. Vol. 34, pp 544-550, and Park, et al (1998) Free Radic. Biol. Med. Vol. 25, pp 79-86] with minor modifications. Briefly, total superoxide dismutase (SOD) activity was measured by monitoring the reduction of cytochrome c at 550 nm in a reaction mixture containing 50 mM potassium phosphate (pH 7.5), 0.1 mM xanthine, 0.5 munit/ml xanthine oxidase, 0.1 mM EDTA, and 10 μM cytochrome c. One unit of SOD represents the enzyme activity that causes a 50% inhibition in the reduction of cytochrome c. Aliquots of samples were taken to determine MnSOD activity by the addition of 5 mM KCN to inhibit CuZnSOD activity [Spitz, et al. (1989) Anal. Biochem. Vol. 179, pp 8-18]. CuZnSOD activity was evaluated by subtracting MnSOD activity from the total SOD activity. Glutathione peroxidase activity was measured by monitoring the oxidation of NADPH at 340 nm in a reaction mixture containing 50 mM potassium phosphate (pH 7.4), 1 mM EDTA, 1 mM $NaN_3$, 0.2 mM NADPH, 1 unit/ml glutathione reductase, and 1 mM GSH. The reaction was started by the addition of 0.25 mM $H_2O_2$. Catalase activity was measured by monitoring the removal of $H_2O_2$ at 240 nm in a reaction mixture containing 50 mM potassium phosphate (pH 7.0) and 10 mM $H_2O_2$. The reduced and oxidized glutathione were measured by using HPLC as previously described [Baek, et al. (2000) J. Cell. Physiol. Vol. 183. pp 100-107; Park, et al. (1998) Free Radic. Biol. Med. Vol. 25, pp 79-86]. Total glutathione contents were expressed as the GSH equivalent to the sum of GSH+2GSSG.

As shown in the left panels of FIG. 1A-1D, MnSOD and CuZnSOD (FIG. 1A), GPX (FIG. 1B), and CAT (FIG. 1C) activities were increased as early as 2 h after irradiation, with a concomitant decrease in total glutathione contents (FIG. 1D). The right panels of FIG. 1A-1D show the patterns of SOD, GPX, CAT, and glutathione changes of the RBC in response to irradiation. Since the mature RBC is devoid of mitochondria, the SOD activity of RBC is primarily that of CuZnSOD. It is evident that changes in the lung and RBC closely resembled each other with the exception of CAT. In general, SOD and GPX activities as well as glutathione levels were higher in lung than in RBC. The levels of CAT activities were similar between the lung and the RBC. However, the CAT activities of RBC did not change in response to radiation during the course of the experiment.

Example 2

This Example illustrates selection, treatment, and statistical methods used in connection with analysis of human patients according to the method of the invention.

Patients with surgically unresectable stage IIIA/IIIB non-small-cell lung cancer (NSCLC) were recruited. Blood samples from patients undergoing concurrent chemo-radiotherapy on Institutional Review Board (IRB)-approved clinical protocols were used for this study. Informed consents were obtained from all patients before registration. To minimize potential confounding factors, only those patients receiving concurrent definitive radiotherapy and paclitaxel-based chemotherapy were included. Patients were excluded if they had received inductive radiotherapy, chemotherapy, or prior thoracic radiotherapy. Patients with unfavorable Eastern Cooperative Oncology Group (ECOG) performance status (2 or greater) or chronic obstructive pulmonary disease (COPD) were also excluded. Staging evaluations included history, physical examination, chest X-ray, and CT with intravenous contrast, including the chest and upper abdomen through the liver and adrenal glands. A total of 15 eligible patients recruited between September 2003 and April 2005 were analyzed in this study.

Thoracic radiotherapy was delivered in 2 Gy daily fractions, 5 fractions a week, over a total treatment time of 6 weeks. Blood samples were collected from patients at baseline and then weekly during the 6-week period of treatment. The samples were centrifuged at 4° C. for 10 min at 1800 g within 1 h upon collection. The cells were washed three times with phosphatebuffered saline, aliquoted, and stored at −80° C. until analyzed. At the time of completion of treatment, serial RBC samples from each patient were analyzed together. Radiation pneumonitis was diagnosed in accordance with the RTOG/EORTC guidelines at 1 and 3 months posttherapy [Cox, et al. (1995) Int J. Radiat. Oncol. BioL Phys. Vol. 31, pp 1341-1346]. It is outlined as follows: grade 0 is no change from baseline; grade 1 is defined as mild symptoms with slight radiographic appearances; grade 2 is defined as moderate symptoms with low grade fever and patchy radiographic appearances; grade 3 is defined as severe symptoms with dense radiographic changes; grade 4 is defined as severe respiratory insufficiencies requiring assisted ventilation. Those grading pneumonitis were blinded to the antioxidant data.

To evaluate the predictive value of each test variable, discriminant analysis was performed [Rao, C. R. *Linear statistical inference and its applications*. New York: Wiley; 1973] by using the computer package SAS (version 8.2). The posterior probability was calculated using the generalized square distance and the multivariate normal distribution with a prior probability of 0.5 for each variable. To evaluate the classification criterion, error-rate estimates were obtained based on the established "leave-one-out" cross-validation method [Lachenbruch, et al. (1968) *Technometrics* Vol. 10, pp 1-10]. This leave-one-out procedure was repeated for every observation and the number of misclassified observations was counted for the error-rate estimate. Sensitivity was calculated as a proportion of patients with pneumonitis who were correctly classified by the crossvalidation. Specificity was calculated as a proportion of patients without pneumonitis who were correctly classified by the cross-validation.

Example 3

This Example provides an analysis of GPX and SOD activities in RBCs of the patients before and during therapy.

To test whether differences in the enzyme activity of the RBCs might be correlated with radiation pneumonitis susceptibility, non-small-cell lung cancer patients receiving concurrent radiotherapy and chemotherapy had serial blood collections before and during treatment. A total of 15 eligible patients were treatment-naive, and had stage III disease with good performance status (0, 1) and normal organ function. The characteristics of these 15 patients are summarized in Table 1. Based on the RTOG/EORTC criteria, 8 patients out of 15 experienced the symptoms of pneumonitis within 3 months after completion of treatment.

TABLE 1

| Characteristics | Number of patients | % |
| --- | --- | --- |
| Number of patients | 15 | 100 |
| Age, years | | |
| Mean | 61 | |
| Range | 44-74 | |
| Sex | | |
| Male | 5 | 33.3 |
| Female | 10 | 66.7 |
| ECOG performance status | | |
| 0 | 7 | 46.7 |
| 1 | 8 | 53.3 |
| AJCC clinical stage | | |
| IIIA | 3 | 20.0 |
| IIIB | 12 | 80.0 |
| Radiation | | |
| Conformal 3D | 8 | 53.3 |
| IMRT[a] | 7 | |
| Chemotherapy | | |
| Yes | 15 | 100.0 |
| Concurrent | 15 | 100.0 |
| Inductive | 0 | 0.0 |

TABLE 1-continued

| Characteristics | Number of patients | % |
| --- | --- | --- |
| Postoperative | 0 | 0.0 |
| No | 0 | 0.0 |
| Pneumonitis | | |
| Yes | 8 | 53.3 |
| Grade 1 | 1 | 6.7 |
| Grade 2 | 3 | 20.0 |
| Grade 3 | 3 | 20.0 |
| Grade 4 | 1 | 6.7 |
| No | 7 | 46.7 |
| Histology | | |
| Adenocarcinoma | 6 | 40.0 |
| Squamous carcinoma | 6 | 40.0 |
| Poorly differentiated | 3 | 20.0 |

[a]IMRT: Intensity-Modulated Radiation Therapy.

Figure 2A:
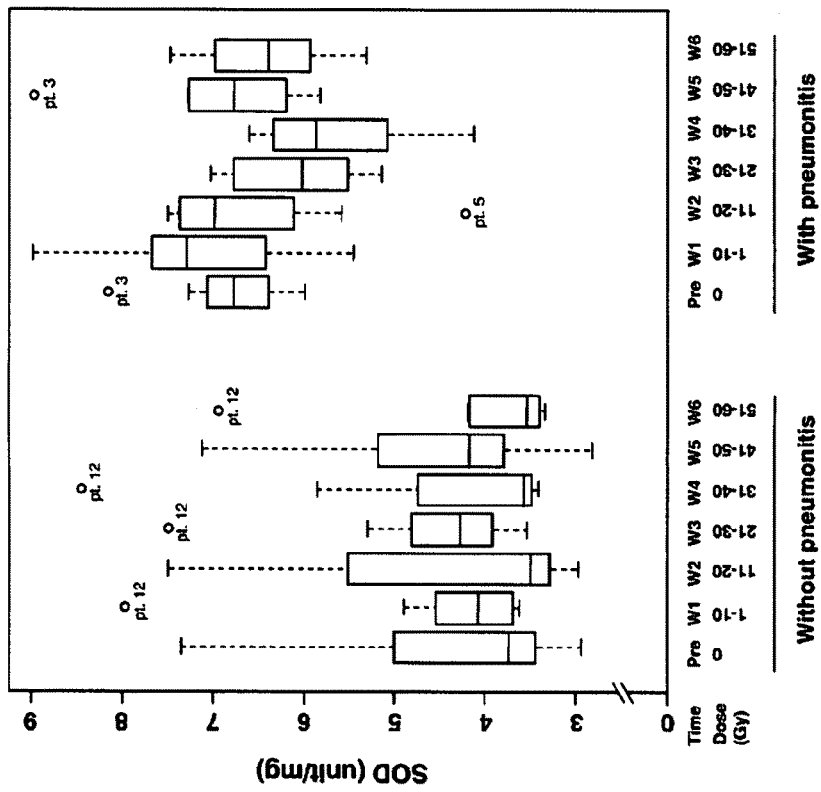

When enzyme activities were analyzed in relation to the presence or absence of pneumonitis, striking differences were revealed. SOD activities were higher in the pneumonitis group (FIG. 2A), while the reverse was true with GPX (FIG. 2B). As shown in Table 2, which presents a comparison of SOD and GPX activities between patients with and without pneumonitis, pretreatment median and ranges of SOD activities were 3.7 (3.4-5.0) in the group without pneumonitis vs 6.8 (6.4-7.1) in the group with pneumonitis (P=0.0192). For GPX, pretreatment activity levels for patients without pneumonitis and those with pneumonitis were 16.5 (14.7-20.6) and 10.7 (10.2-14.8), respectively (P=0.0379). These differences remained through each week of treatment.

TABLE 2

| Variable | Time | Without pneumonitis | With pneumonitis | P value[a] |
| --- | --- | --- | --- | --- |
| | Median SOD activity (range) from n evaluable patients | | | |
| SOD | Pre | 3.7 (3.4-5.0) n = 7 | 6.8 (6.4-7.1) n = 7 | 0.0192 |
| | Week 1 | 4.1 (3.7-4.5) n = 7 | 7.3 (6.4-7.7) n = 8 | 0.0140 |
| | Week 2 | 3.5 (3.3-5.5) n = 7 | 7.0 (6.1-7.4) n = 8 | 0.0541 |
| | Week 3 | 4.3 (3.9-4.8) n = 7 | 6.0 (5.5-6.8) n = 8 | 0.0277 |
| | Week 4 | 3.6 (3.5-4.7) n = 7 | 5.9 (5.1-6.3) n = 8 | 0.0721 |
| | Week 5 | 4.2 (3.8-5.2) n = 7 | 6.8 (6.2-7.3) n = 7 | 0.0128 |
| | Week 6 | 3.5 (3.4-4.2) n = 5 | 6.4 (5.9-7.5) n = 6 | 0.0519 |
| | Median GPX activity (range) from n evaluable patients | | | |
| GPX | Pre | 16.5 (14.7-20.6) n = 7 | 10.7 (10.2-14.8) n = 7 | 0.0379 |
| | Week 1 | 19.4 (15.2-22.5) n = 7 | 11.9 (10.3-14.1) n = 8 | 0.0059 |
| | Week 2 | 18.4 (16.7-22.5) n = 7 | 11.2 (9.9-13.7) n = 8 | 0.0022 |
| | Week 3 | 19.1 (15.1-22.5) n = 7 | 11.4 (10.2-11.5) n = 8 | 0.0093 |
| | Week 4 | 18.1 (15.1-24.7) n = 7 | 11.6 (10.9-12.1) n = 8 | 0.0264 |
| | Week 5 | 18.2 (16.3-22.3) n = 7 | 11.8 (11.5-12.3) n = 7 | 0.0175 |
| | Week 6 | 23.0 (14.8-23.8) n = 5 | 13.2 (12.0-13.4) n = 6 | 0.1255 |

[a]P values were obtained by the Wilcoxon two-sample test.

Figures 3A, 3B:
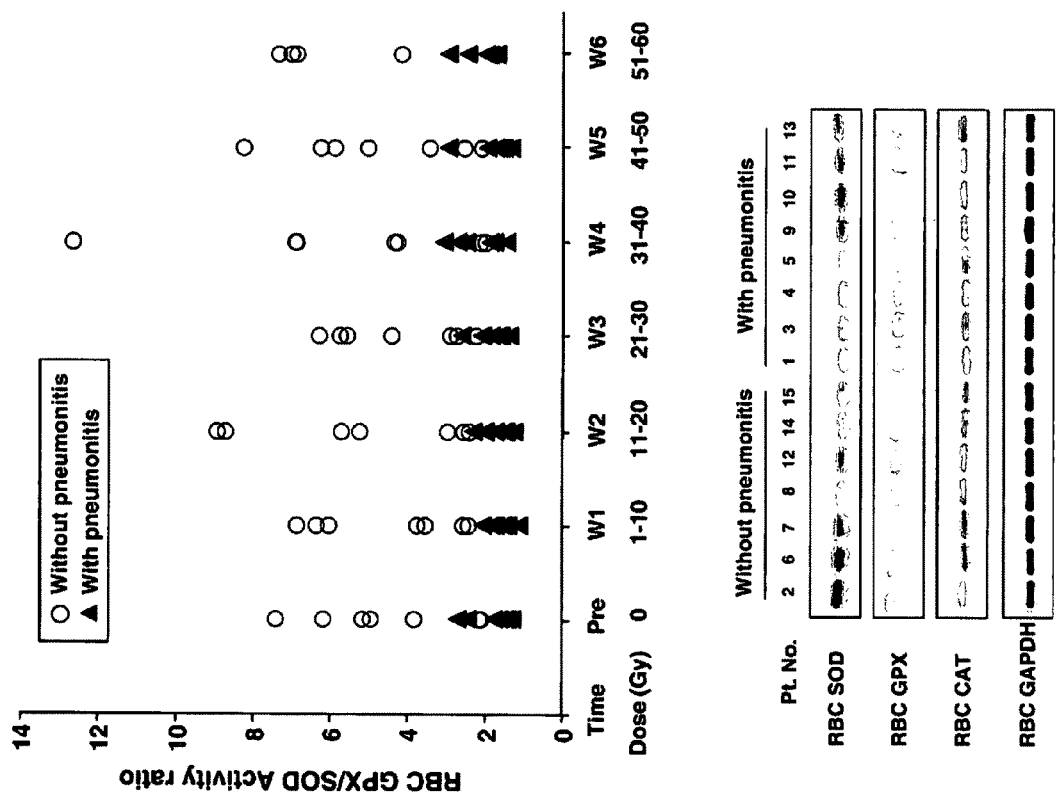
FIG. 3A provides a graphical representation of the distribution of the GPX/SOD ratio of the lung cancer patients. The ratio of GPX/SOD activity was plotted before (pre) and during the treatment (FIG. 3A). Open circle, patients without pneumonitis; closed triangle, patients with pneumonitis.
FIG. 3B provides a photographic representation of the amounts of SOD, GPX, and CAT proteins as probed by Western blot analysis. Equal amounts of proteins (50 μg for SOD, 100 μg for GPX, and 80 μg for CAT) from pretreatment RBC samples were analyzed. A total of 30 μg was used for GAPDH Western blot as a loading control.

The Week 2, 4, and 6 values of SOD activities and the Week 6 value of GPX barely missed statistical significance. Because high levels of SOD and low levels of GPX activities were associated with pneumonitis development, we next examined the ratio of GPX/SOD activities between the two groups. The results were even more striking (pretreatment P=0.0046). As shown in FIG. 3A, a significant difference between the two groups can be easily visualized. Because the difference in SOD and GPX activities between the two groups was detected from the beginning, we tested whether this was also reflected in the steady-state protein levels of these enzymes. The treatment per se did not cause any appreciable changes of SOD or GPX activities. As shown in the Western blot data of FIG. 3B, the amount of SOD, GPX, or CAT proteins present in RBCs did not differ significantly among patients with or without pneumonitis. These Western blot analysis were performed using protein extracts from the patients' RBCs analyzed in duplicate by SDS-polyacrylamide gel electrophoresis using standard techniques and commercially available reagents.

Glutathione is a major small antioxidant molecule. The level of glutathione has been shown to influence the acute radiation effect in animals and humans [Park, et al. (2001) *J. Biol. Mol. Biochem.* Vol. 34, pp 544-550; Bhattathiri, et al. (1994) *Int J. Radiat. Oncol. Biol. Phys.* Vol. 29, pp 383-386]. We did not find a statistically significant difference in the dynamics of GSH or GSSG changes or in CAT activity between the two groups (data not shown).

Example 4

This Example provides an analysis of the sensitivity and specificity of the present invention in predicting susceptibility to pneumonitis in human patients who are treated with RT.

To evaluate the classification (without pneumonitis vs with pneumonitis) performance of SOD and GPX activities or the ratio of GPX/SOD, the discriminant analysis was performed [Rao, C. R. *Linear statistical inference and its applications.* New York: Wiley; 1973]. To evaluate the classification criterion, error-rate estimates were obtained based on the leave-one-out cross-validation [Lachenbruch, et al. (1968) *Technometrics* Vol. 10, pp 1-10]. The classification capacities of each variable are shown in Table 3 which presents test performance characteristics of SOD and GPX activities, as well as the relative ratio of the GPX/SOD activity. Statistical significance of the variables was calculated using the likelihood ratio criterion. The smaller P values of GPX/SOD ratio than those of SOD or GPX activities indicated a greater discriminating power of the GPX/SOD ratio than SOD or GPX activity alone. Sensitivity and specificity of the classification performance are also shown in Table 3.

TABLE 3

| Variable | Time | N | Sensitivity (%) | Specificity (%) | Overall error (%) | P value[a] |
|---|---|---|---|---|---|---|
| SOD | Pre | 14 | 85.7 | 71.4 | 21.4 | 0.0038 |
| | Week 1 | 15 | 87.5 | 85.7 | 13.4 | 0.0026 |
| | Week 2 | 15 | 75.0 | 71.4 | 26.8 | 0.0155 |
| | Week 3 | 15 | 87.5 | 85.7 | 13.4 | 0.0226 |
| | Week 4 | 15 | 87.5 | 71.4 | 20.1 | 0.1705 |
| | Week 5 | 14 | 100.0 | 71.4 | 14.3 | 0.0051 |
| | Week 6 | 11 | 83.3 | 80.0 | 18.3 | 0.0148 |
| GPX | Pre | 14 | 71.4 | 71.4 | 28.6 | 0.0360 |
| | Week 1 | 15 | 87.5 | 71.4 | 20.5 | 0.0028 |
| | Week 2 | 15 | 87.5 | 71.4 | 20.5 | 0.0028 |
| | Week 3 | 15 | 87.5 | 85.7 | 13.4 | 0.0025 |
| | Week 4 | 15 | 87.5 | 57.1 | 27.7 | 0.0284 |
| | Week 5 | 14 | 85.7 | 71.4 | 21.4 | 0.0136 |
| | Week 6 | 11 | 83.3 | 60.0 | 28.3 | 0.0507 |
| GPX/SOD | Pre | 14 | 85.7 | 71.4 | 21.4 | 0.0046 |
| | Week 1 | 15 | 100.0 | 100.0 | 0.0 | 0.0009 |
| | Week 2 | 15 | 100.0 | 71.4 | 14.3 | 0.0058 |
| | Week 3 | 15 | 87.5 | 85.7 | 13.4 | 0.0018 |
| | Week 4 | 15 | 87.5 | 71.4 | 20.5 | 0.0233 |
| | Week 5 | 14 | 85.7 | 71.4 | 21.4 | 0.0058 |
| | Week 6 | 11 | 83.3 | 80.0 | 18.3 | 0.0098 |

[a] P values were obtained by F statistics based on Wilk's Lambda.

Since the differences in SOD and GPX activities predict the risk of pneumonitis development before the start of treatment, we tested whether the repeated measurements of activities of these enzymes during treatment improve the predictive value. To this end, the frequency of higher SOD levels compared with the median pretreatment value up to a specified week was analyzed using the logistic regression. Similarly, the frequency of the lower GPX levels than the median pretreatment value was analyzed in a univariate manner. A model fit statistic called Akaike information criterion (AIC) was examined where the smaller value indicates the better model fitting [24]. The AIC of SOD was found to decrease at Week 1 (from pretreatment value of 18.7 to 15.8), but increased slightly at Week 2 (16.4) and Week 3 (17.4). In the case of GPX, the AIC was decreased gradually until Week 3, but the degree of AIC decrease was smaller after the Week 2 (pretreatment, 21.4; Week 1, 19.1; Week 2, 16.4; Week 3, 15.8). When the GPX/SOD ratio was tested, a quasi-complete separation of the data points occurred at Week 1; i.e., the incidence of pneumonitis was completely separated by the GPX/SOD ratio with an exception of a single GPX/SOD value. Therefore, surveillance up to the Week 1 or 2 following the start of treatment may be sufficient to predict pneumonitis.

The invention has been described through specific embodiments. However, routine modifications to the compositions, methods and devices will be apparent to those skilled in the art and such modifications are intended to be covered within the scope of the invention.

The invention claimed is:

1. A method for determining whether an individual is likely to be susceptible to radiation pneumonitis comprising:
    determining in a red blood cell sample obtained from the individual enzymatic activity of glutathione peroxidase (GPX), or enzymatic activity of superoxide dismutase (SOD), or a ratio of GPX and SOD enzymatic activity, wherein:
    determining an SOD enzymatic activity that is higher than a normal control indicates that the individual is likely to be susceptible to radiation pneumonitis;
    determining an SOD enzymatic activity that is not higher than a normal control is indicative that the individual is likely not to be susceptible to radiation pneumonitis;
    determining a GPX enzymatic activity that is lower than a normal control is indicative that the individual is likely to be susceptible to radiation pneumonitis;
    determining a GPX enzymatic activity that is not lower than a normal control is indicative that the individual is likely not to be susceptible to radiation pneumonitis;
    determining a ratio of GPX enzymatic activity to SOD enzymatic activity that is lower than a normal control is indicative that the individual is likely to be susceptible to radiation pneumonitis; and/or
    determining a ratio of GPX enzymatic activity to SOD enzymatic activity that not lower than a normal control is indicative that the individual is likely not to be susceptible to radiation pneumonitis.

2. The method of claim 1, wherein a ratio of about 0.5 GPX/SOD activity or lower is indicative that an individual is at risk for developing radiation pneumonitis.

3. The method of claim 1, wherein the individual has been diagnosed with or is suspected of having a solid tumor.

4. The method of claim 3, wherein the solid tumor is selected from the group consisting of prostate, breast, colorectal, lung (small cell and non-small cell), ovarian, melanoma, urinary system, uterine, endometrial, pancreatic, head and neck, oral cavity, thyroid, stomach, nervous system, liver, and esophageal tumors, and wherein the solid tumor has metastasized to the individual's thorax.

5. The method of claim 1, wherein the individual has been diagnosed with or is suspected of having a hematological cancer.

6. The method of claim 5, wherein the hematological cancer is selected from the group consisting of Hodgkins Lymphoma, Non-Hodgkins Lymphoma, leukemias, and myelomas.

7. The method of claim 5, wherein the individual is a candidate for a bone marrow transplant.

8. The method of claim 1, wherein the red blood cells are obtained from the individual prior to radiation therapy.

9. The method of claim 1, wherein the red blood cells are obtained from the individual during a course of radiation therapy.

10. The method of claim 1, wherein:
   the normal control for SOD enzymatic activity is an average SOD enzymatic activity determined from a plurality of individuals who were treated with radiation therapy and did not develop radiation pneumonitis;
   wherein the normal control for GPX enzymatic activity is an average GPX activity determined from a plurality of individuals who were treated with radiation therapy and did not develop radiation pneumonitis; and
   wherein the normal control for the ratio of GPX enzymatic activity to SOD enzymatic activity is an average ratio of GPX enzymatic activity to SOD enzymatic activity determined from a plurality of individuals who were treated with radiation therapy and did not develop radiation pneumonitis.

11. A method for determining a treatment regime for an individual or treating an individual who is diagnosed with or suspected of having cancer comprising:
   determining in a red blood cell sample obtained from the individual the enzymatic activity of glutathione peroxidase (GPX), or determining the enzymatic activity superoxide dismutase (SOD), or determining a ratio of GPX and SOD activity;
   wherein if:
   a GPX activity that is lower than a normal control is determined; or
   an SOD activity that is higher than a normal control is determined; or
   a ratio of GPX activity to SOD activity that is lower than a normal control is determined,
   the individual is recommended for treatment and/or treated with at least one treatment selected from the group consisting of: radiation therapy using a radiation dosage that is less than a radiation dosage used for an individual who is not likely to be susceptible to radiation pneumonitis; intensity-modulated radiotherapy (IMRT); IMRT with respiratory-gating; stereotactic radiotherapy; particle-beam therapy with protons; helical tomotherapy; and, administration of a radiation protector medication;
   and wherein if:
   a GPX activity that is the same as or higher than a normal control is determined; or
   an SOD activity that is the same as or lower than a normal control is determined; or
   a ratio of GPX activity to SOD activity that is the same as or higher than a normal control is determined,
   the individual is recommended for and/or treated with radiation therapy using a radiation dosage of at least 80 Gy.

12. The method of claim 11, wherein the ratio of GPX activity to SOD activity that is lower than a normal control is a ratio of about 0.5 GPX/SOD.

13. The method of claim 11, wherein the individual has been diagnosed with or is suspected of having a solid tumor.

14. The method of claim 13, wherein the solid tumor is selected from the group consisting of prostate, breast, colorectal, small cell lung, non-small cell lung, ovarian, melanoma, urinary system, uterine, endometrial, pancreatic, head and neck, oral cavity, thyroid, stomach, nervous system, liver, and esophageal tumors, and wherein the solid tumor has metastasized to the individual's thorax.

15. The method of claim 11, wherein the individual has been diagnosed with or is suspected of having a hematological cancer.

16. The method of claim 15, wherein the hematological cancer is selected from the group consisting of Hodgkins Lymphoma, Non-Hodgkins Lymphoma, leukemias, and myelomas.

17. The method of claim 15, wherein the individual is a candidate for a bone marrow transplant.

18. The method of claim 11, wherein:
   the normal control for SOD enzymatic activity is an average SOD enzymatic activity determined from a plurality of individuals who were treated with radiation therapy and did not develop radiation pneumonitis;
   wherein the normal control for GPX enzymatic activity is an average GPX activity determined from a plurality of individuals who were treated with radiation therapy and did not develop radiation pneumonitis; and
   wherein the normal control for the ratio of GPX enzymatic activity to SOD enzymatic activity is an average ratio of GPX enzymatic activity to SOD enzymatic activity determined from a plurality of individuals who were treated with radiation therapy and did not develop radiation pneumonitis.

19. The method of claim 11, wherein the radiation protector medication is selected from the group consisting of amifostine, angiotensin-converting enzyme inhibitors, pentoxifylline, melatonin, and combinations thereof.

20. The method of claim 11, wherein the dosage of at least 80 Gy is a dosage of from 80 Gy to 100 Gy, and wherein the radiation dosage that is less than a radiation dosage used for an individual who is not likely to be susceptible to radiation pneumonitis is a dosage of 60 Gy or less.

* * * * *